United States Patent
Booty, Jr. et al.

(10) Patent No.: US 7,431,689 B2
(45) Date of Patent: Oct. 7, 2008

(54) METHOD AND APPARATUS TO RELAX A PATIENT TO MINIMIZE THE ADMINISTRATION OF ANESTHESIA, FACILITATE SUCCESSFUL SURGERY, AND SHORTEN RECOVERY TIME

(75) Inventors: Donald J. Booty, Jr., Cave Creek, AZ (US); Alice H. Cash, 3219 Marion Ct., Louisville, KY (US) 40206

(73) Assignee: Alice H. Cash, Louisville, KY (US)

( * ) Notice: Subject to any disclaimer, the term of this patent is extended or adjusted under 35 U.S.C. 154(b) by 0 days.

(21) Appl. No.: 11/526,895

(22) Filed: Sep. 22, 2006

(65) Prior Publication Data

US 2007/0112245 A1    May 17, 2007

Related U.S. Application Data

(60) Provisional application No. 60/720,770, filed on Sep. 26, 2005.

(51) Int. Cl.
*A61M 21/00* (2006.01)

(52) U.S. Cl. .......................... 600/27; 128/898

(58) Field of Classification Search .............. 5/601; 600/500, 587, 546, 554, 481, 485, 26, 27, 600/28, 21; 128/897–899, 204.23, 204.18; 434/185, 116; 381/60
See application file for complete search history.

(56) References Cited

U.S. PATENT DOCUMENTS

| | | | |
|---|---|---|---|
| 5,304,112 A * | 4/1994 | Mrklas et al. | 600/27 |
| 5,318,503 A * | 6/1994 | Lord | 600/27 |
| 5,403,263 A * | 4/1995 | Rodgers | 600/28 |
| 5,993,046 A * | 11/1999 | McGrady et al. | 700/231 |
| 6,123,661 A * | 9/2000 | Fukushima et al. | 600/27 |
| 6,275,340 B1 * | 8/2001 | Brown | 359/630 |
| 6,315,736 B1 * | 11/2001 | Tsutsumi et al. | 600/500 |
| 6,641,522 B2 * | 11/2003 | August | 600/27 |
| 6,641,523 B2 * | 11/2003 | Ashenden | 600/28 |
| 2005/0235422 A1 * | 10/2005 | Wallace | 5/601 |

FOREIGN PATENT DOCUMENTS

GB          2330445 A  *  4/1999

* cited by examiner

*Primary Examiner*—Charles A. Marmor, II
*Assistant Examiner*—Christine D Hopkins
(74) *Attorney, Agent, or Firm*—Stites & Harbison, PLLC; David W. Nagle, Jr.; Robert C. Yang

(57) ABSTRACT

A musical method and apparatus for minimizing the amount of anesthetic required during surgery and for shortening the recovery time after surgery.

9 Claims, 7 Drawing Sheets

METHOD AND APPARATUS TO RELAX A PATIENT TO MINIMIZE THE ADMINISTRATION OF ANESTHESIA, FACILITATE SUCCESSFUL SURGERY, AND SHORTEN RECOVERY TIME

This application claims priority based on Provisional Patent Application No. 60/720,770, filed Sep. 26, 2005.

This invention relates to procedures for facilitating the sequencing of an individual through a series of related or unrelated events.

More particularly, the invention relates to a process for facilitating the sequencing of a patient through pre-op, surgery, post-op, and recovery.

In a further respect, the invention relates to a process for minimizing the amount of anesthesia that is administered to a patient for surgery and for reducing the recovery time for a patient.

Reducing the amount of anesthesia required by an individual during surgery tends to reduce the time required for a patient to regain consciousness and progress toward full recovery. Further, since some patients have unexpected or unpredictable adverse reactions to certain anesthesias, reducing the amount of anesthesia administered to a patient likely reduces unforeseen and adverse reactions.

Accordingly, it would be highly desirable to provide processes that reduce the amount of anesthesia required by a patient and that also speed recovery of the patient.

Therefore, it is a principal object of the instant invention to provide an improved process to minimize the quantity of anesthesia administered to a patient and to facilitate a successful surgery and recovery.

These and other, further and more specific objects and advantages of the invention will be apparent to those of skill in the art from the following detailed description thereof, taken in conjunction with the drawings, in which.

Figure 1:
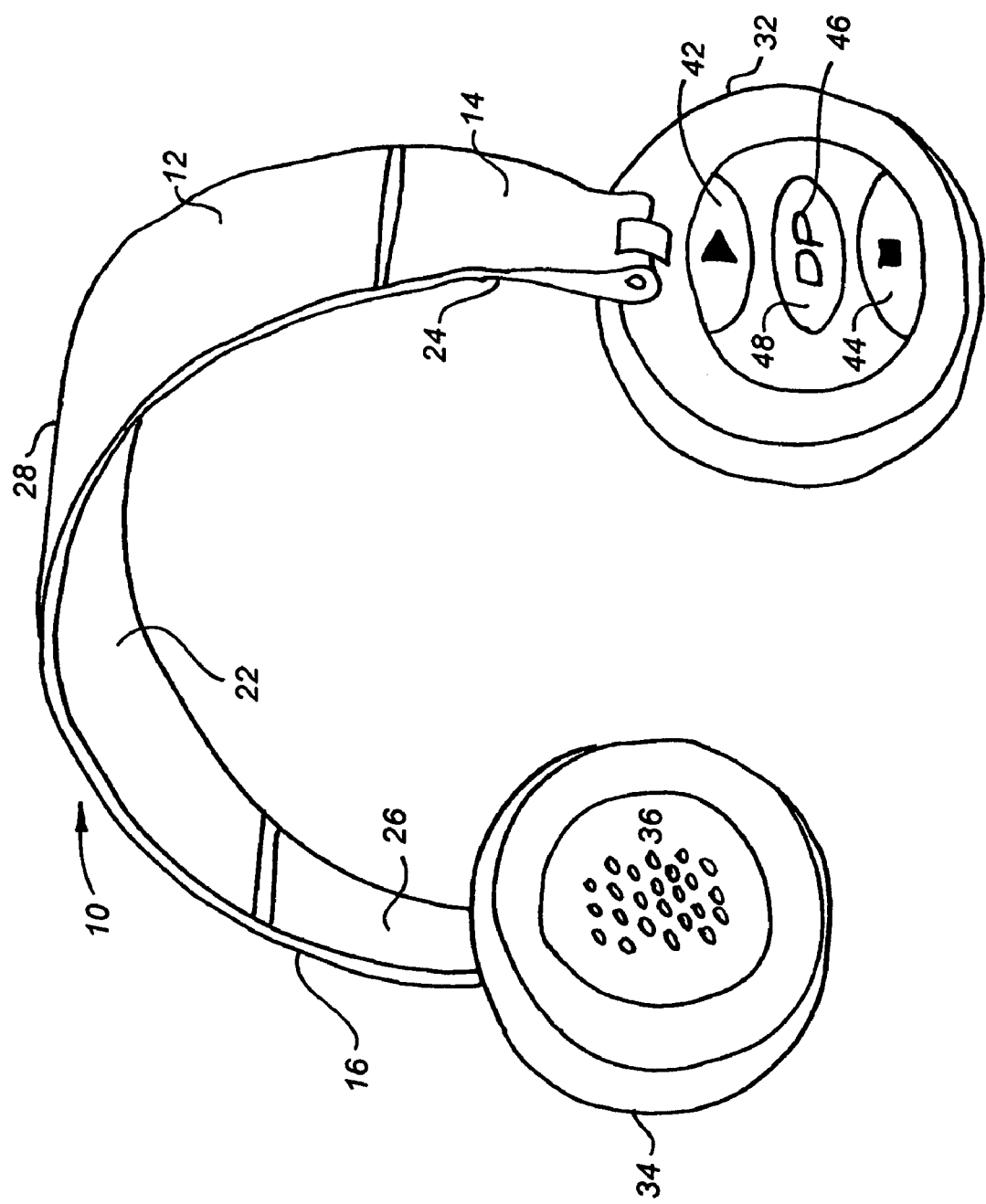
FIG. 1 is a perspective view illustrating headphones utilized in the practice of the invention.

Briefly, in accordance with the invention, we provide an improved method to minimize the amount of anesthesia required during surgery on an individual by at least one surgeon, comprising the steps of determining the normal heart rate and normal respiration rate of the individual; identifying primary music that, when the individual is reclining, produces a first selected reduced heart rate less than the normal heart rate, and a second selected reduced respiration rate less than the normal respiration rate; and, playing for the individual the primary music while the individual is held in a pre-surgery area.

In a further embodiment of the invention, we provide an improved method to minimize the amount of anesthesia required during surgery on an individual by at least one surgeon. The method comprises the steps of determining an average range of heart rate and an average range of respiration rate of the individual; identifying primary music that, when the individual is reclining, produce a first selected reduced heart rate less than the average range of heart rate and a second selected reduced respiration rate less than the average range of respiration rate; and, playing for the individual the primary music while the individual is held in a pre-surgery area. Additional steps can be carried out comprising the step of identifying secondary music that, when the individual is reclining, produces a second selected reduced heart rate less than the first selected reduced heart rate, more specifically, if desired, to a target range of a minimum of 40 and a maximum of 80 heartbeats per minute (or another desired target range). This range can, if desired, but not necessarily, be altered or adjusted depending on any particular selected variable. For example, as an individual's age increases, the range may decrease to a minimum of 30 and a maximum of 70. Other variables that can be used include the individual's overall health including cardiovascular health, type of surgery being performed, etc. A further additional step that can be carried out includes identifying secondary music that produces a second selected respiration rate less than the first selected respiration rate and that is in a desired target range such as, by way of example and not limitation, a target range of approximately 14 to 16 breaths (inhalation and exhalation) per minute. This range can, if desired, but not necessarily, be altered or adjusted depending on any particular selected variable. For example, as an individual's age increases, the range may decrease to 13 to 15 breaths per minute. Other variables that can be used include the individual's overall health, type of surgery being performed, etc. Secondary music can be played for the individual the secondary music while the individual undergoes surgery. Still additional steps can be carried out comprising the steps of, while the individual is in surgery, playing the secondary music for the individual out of ear shot of the surgeon; and, playing music other than the secondary music for the surgeon out of ear shot of the individual. The individual can wear headphones that produce said primary music and said secondary music. The headphones can repeat said primary music and said secondary music. The primary music can be discontinued and the playing of the secondary music initiated while the individual is moved from pre-surgery to surgery. The secondary music can be discontinued and the tertiary music initiated when the individual is moved from surgery to post surgery.

In another embodiment of the invention, we provide an improved method to minimize the amount of anesthesia required during surgery on an individual having voluntary and involuntary muscles. The method comprises the step of playing for the individual while the individual is held in a pre-surgery area music that slows the individual's heart beat and respiration in comparison to the individual's heat beat and respiration prior to entering the pre-surgery area; and, increases disengagement of the individual's voluntary muscles.

In a further embodiment of the invention, we provide an improved method to minimize the amount of anesthesia required during surgery on an individual having voluntary and involuntary muscles. The method comprises the steps of playing for the individual a first relaxing musical performance when the individual is in a pre-surgery area; when the individual is in surgery, a second relaxing musical performance different from the first musical performance; and, when the individual is in a post-surgery area, a third upbeat musical performance different from the first and second musical performances.

In still another embodiment of the invention, we provide a system to minimize the amount of anesthesia required during surgery on an individual having voluntary and involuntary muscles. The system comprises audio apparatus to play music for the individual in pre-surgery and during surgery music, said music including a first musical performance played in pre-surgery and a second musical performance played during surgery and different than the first musical performance; and, apparatus for automatically terminating at a selected station the first musical performance and playing the second musical performance when the individual is moved from pre-surgery to surgery.

In yet another embodiment of the invention, we provide an improved method to minimize the amount of anesthesia required during surgery on an individual to facilitate the lowering of blood pressure. The method comprises the step of playing for the individual while the individual is held in a pre-surgery area music that slows the individual's heart beat and respiration in comparison to the individual's heat beat and respiration prior to entering the pre-surgery area; increases disengagement of the individual's voluntary muscles; and lowers the blood pressure.

In a yet further embodiment of the invention, we provide an improved method to minimize the amount of anesthesia required during surgery on an individual to facilitate the lowering of blood pressure. The method comprises the steps of playing for the individual a first relaxing musical performance when the individual is in a pre-surgery area; when the individual is in surgery, a second relaxing musical performance different from the first musical performance; and, when the individual is in a post-surgery area, a third upbeat musical performance different from the first and second musical performances.

In yet another embodiment of the invention, we provide a system to minimize the amount of anesthesia required during surgery on an individual to facilitate the lowering of blood pressure. The system comprises audio apparatus to play music for the individual in pre-surgery and during surgery music, said music including a first musical performance played in pre-surgery and a second musical performance played during surgery and different than the first musical performance; and, apparatus for automatically terminating at a selected station the first musical performance and playing the second musical performance when the individual is moved from pre-surgery to surgery.

Turning now the drawings, which depict the presently preferred embodiments of the invention for the purpose of illustration thereof, and not by way of limitation of the invention, and in which like characters refer to corresponding elements throughout the several views, FIG. 1 illustrates a headphone having a first outer surface 12 and a first inner surface 22. Surface 12 includes second and third outer surfaces 14 and 16. Surface 22 includes second and third inner surfaces 24 and 26. Surfaces 12, 14, 16, 22, 24 and 26 comprise the headband assembly. The length of the headband can be, if desired, adjustable.

Headphones 10 also include an integral pivotable (on the headband) right earphone assembly 32; an integral pivotable (on the headband) left earphone assembly 34. Holes 36 on the interior of assembly 34 permit music to emanate from assembly 34 outwardly therethrough. Function keys 42 and 44 on the right assembly 32 control the playback and stop modes, respectively. LCD display 46 shows the music channel currently playing: "Pre-Op", "OP" (surgery), "Post-Op", or "GR" (general recovery). Headphones 10 can be constructed in any desired manner and can be, by way of example, electrostatic, electret, 4-channel, etc.

Figure 2:
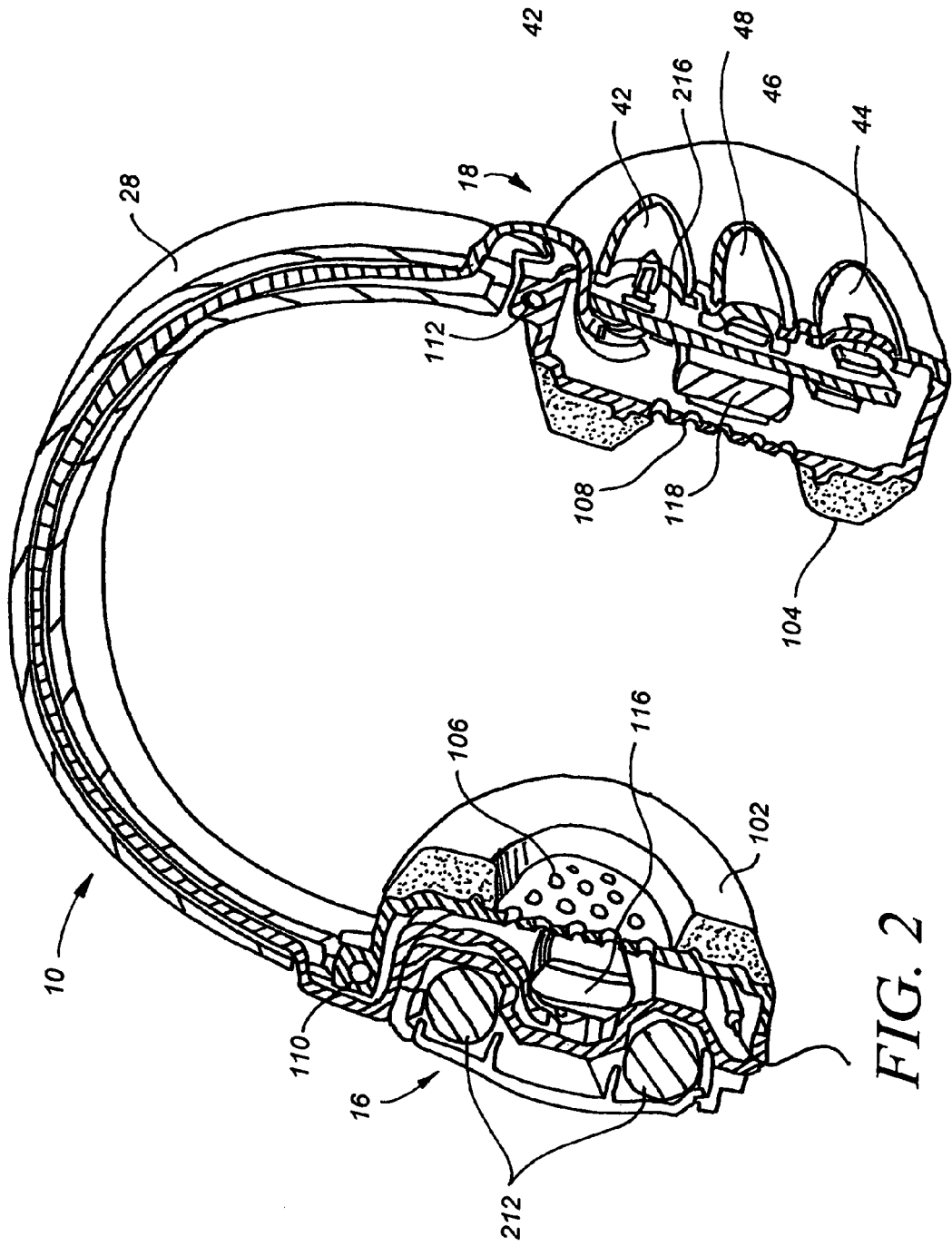
FIG. 2 is a partial section view of the headphones of FIG. 1 illustrating further construction details thereof.

In FIG. 2, headphones 10 include a power source consisting of one or more batteries 212. Batteries 212 power integrated circuit (IC) 214 on printed circuit board (PCB) 216. IC 214 includes electronic chip 218 to store pre-recorded music. IC 214 includes other well known electronic components required to operate headphones in the manner described herein. When music is played by headphones 10, music emanates from small transducers 116 and 118 located in earphones 16 and 18, respectively. The reader skilled in the art will understand that the construction of headphones 10 as presented is but one means possible, and that other means possible do not modify in any way the scope of the invention.

Operation of headphones 10 is accomplished using keys 42 and 44. Once the play button 42 is pressed, music in headphones plays. The music for the particular station (pre-op, op, post-op, general recovery) plays completely through, start over, plays completely through, starts over, etc. The music continues "looping" in this fashion until the stop button 44 is pressed, or, until button 42 is pressed to index to the music for one of the next stations.

If button 42 is initially pressed once, "PRE-OP" appears in display 46 to indicate that pre-op music is continuously playing and "looping" until the stop button 44 is pressed or until the button 42 is pressed again one or more times to cycle the music selection from "PRE-OP" to "OP" or "POST-OP" or "GENERAL RECOVERY" or back to "PRE-OP".

If button 42 is initially pressed twice in quick succession, "OP" appears in display 46 to indicate that op music is continuously playing and "looping" until the stop button 44 is pressed or until button 42 is pressed again one or more times to cycle the music selection from "OP" to "POST OP" or "GENERAL RECOVERY" or "PRE-OP".

If button 42 is initially pressed three times in quick succession, "POST-OP" appears in display 46 to indicate that post-op music is continuously playing and "looping" until the stop button 44 is pressed or until button 42 is pressed again one or more times to cycle the music selection from "POST-OP" to "GENERAL RECOVERY" or "PRE-OP" or "OP", or even back to "POST-OP".

If button 42 is initially pressed four times in quick succession, "GENERAL RECOVERY" appears in display 46 to indicate that general recovery music is continuously playing and "looping" until the stop button 44 is pressed or until button 42 is pressed one or more times to cycle the music selection to the desired "station" (i.e., "PRE-OP", "OP", etc.).

Ordinarily, when a patient enters pre-op, button 42 is pressed one or more times until "PRE-OP" appears on display 46. This causes the music associated with pre-op to play. When the patient is being moved from pre-op to op, button 42 is pressed once to cause "OP" to appear on display 46 and to cause the music to play that was selected for surgery. When the patient is being moved from surgery to post-op, button 42 is pressed once again to cause "POST-OP" to appear on display 46 and to cause the music to play that was selected for post-op. And, finally, when the patient is being moved from post-op to general recovery, button 42 is pressed once to cause "GENERAL RECOVERY" to appear on display 46 and to cause the music to play that was selected for general recovery.

The reader skilled in the art will readily understand that the above sequence describes only one of many possible electronic input formats for the control of headphones 10, including function controls for forward and/or reverse cycling through the music tracks.

Figure 3:
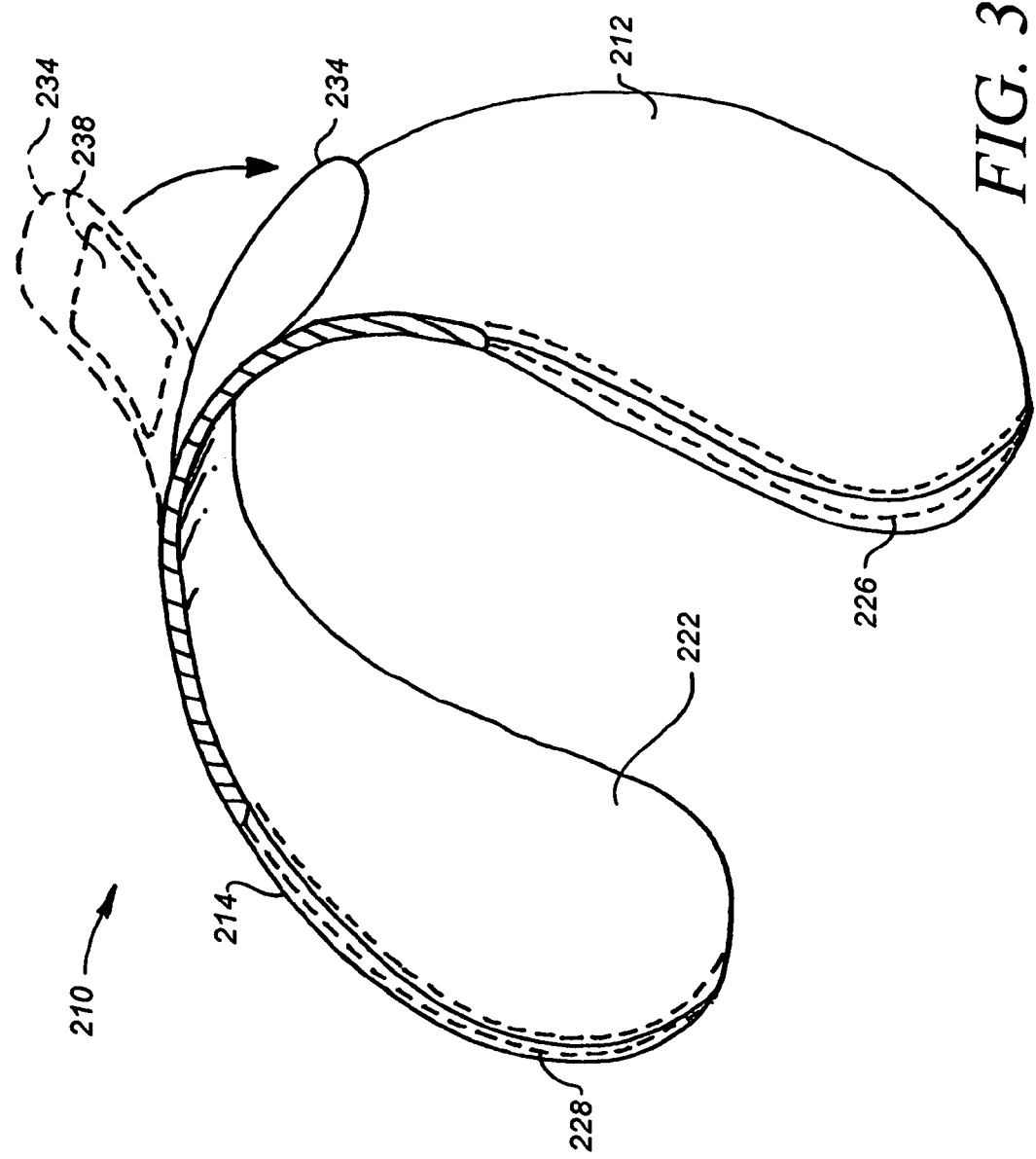
FIG. 3 is a perspective view illustrating a cover for the headphones of FIG. 1.
Figure 4:
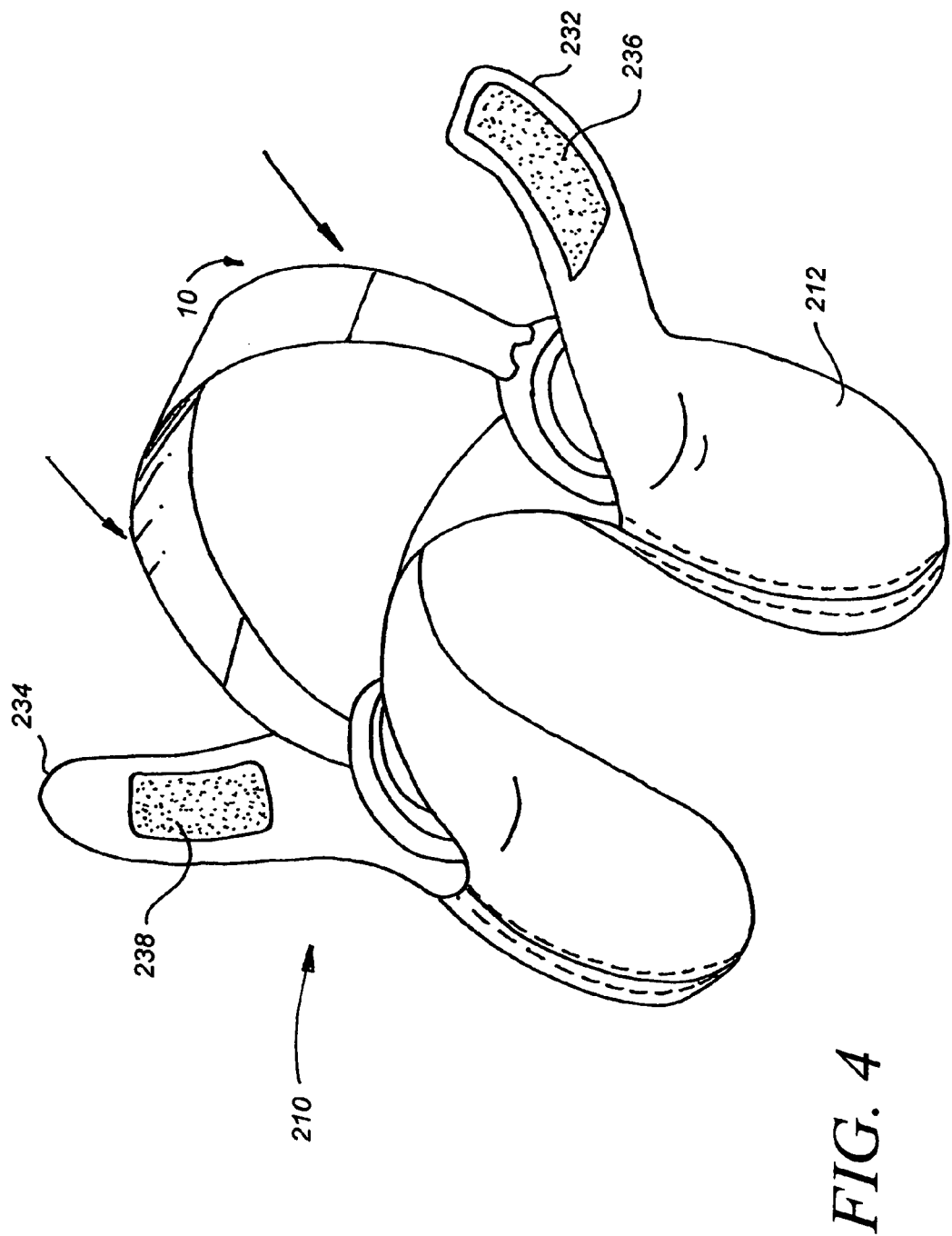
FIG. 4 is a perspective view of the cover of FIG. 3 illustrating the insertion of headphones therein.

In FIG. 3, cover 210 includes first fabric part 212, second fabric part 214, third fabric part 222, and sewn seams 226 and 228 that bind together the three fabric parts 212, 214, 222. Flap 234 includes one end secured to part 214. VELCRO 238 on the other end of flap 234 secures flap 234 to VELCRO 236 on flap 232 (FIG. 4) of part 212.

Cover 210 preferably is soft and pliable and readily conforms to headphones 10. Any desired fabric material can be utilized to fabricate cover 210, including SUPREL, ACTUREL, TYVEK, CRYPTON, and fabric impregnated with AgION. Cover 10 may be used once, or cleaned and sterilized and reused.

Figure 5:
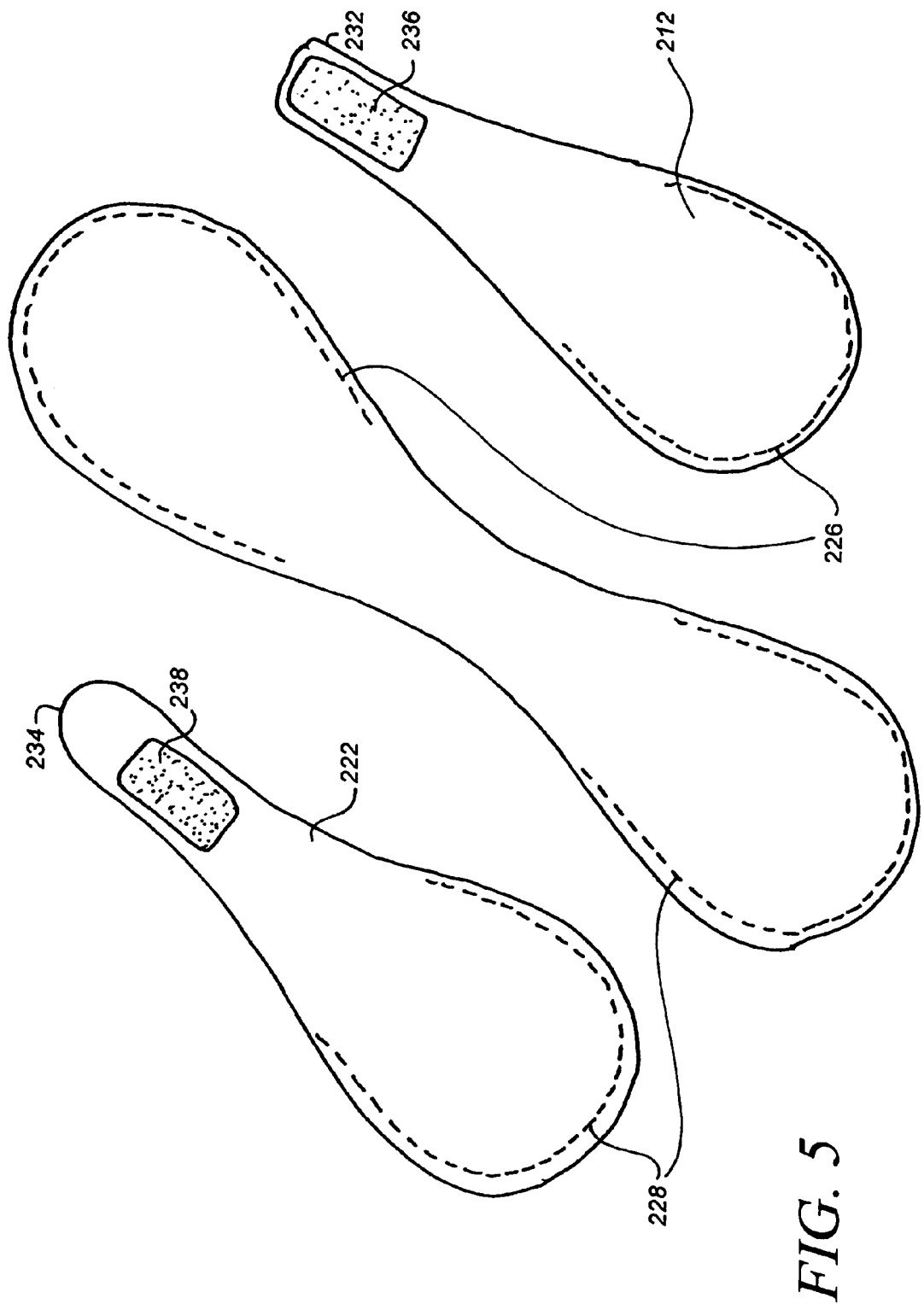
FIG. 5 is an exploded view of the fabric parts and other components that form the cover of FIG. 3.

FIG. 5 is an exploded view of components of cover 10.

Figure 6:
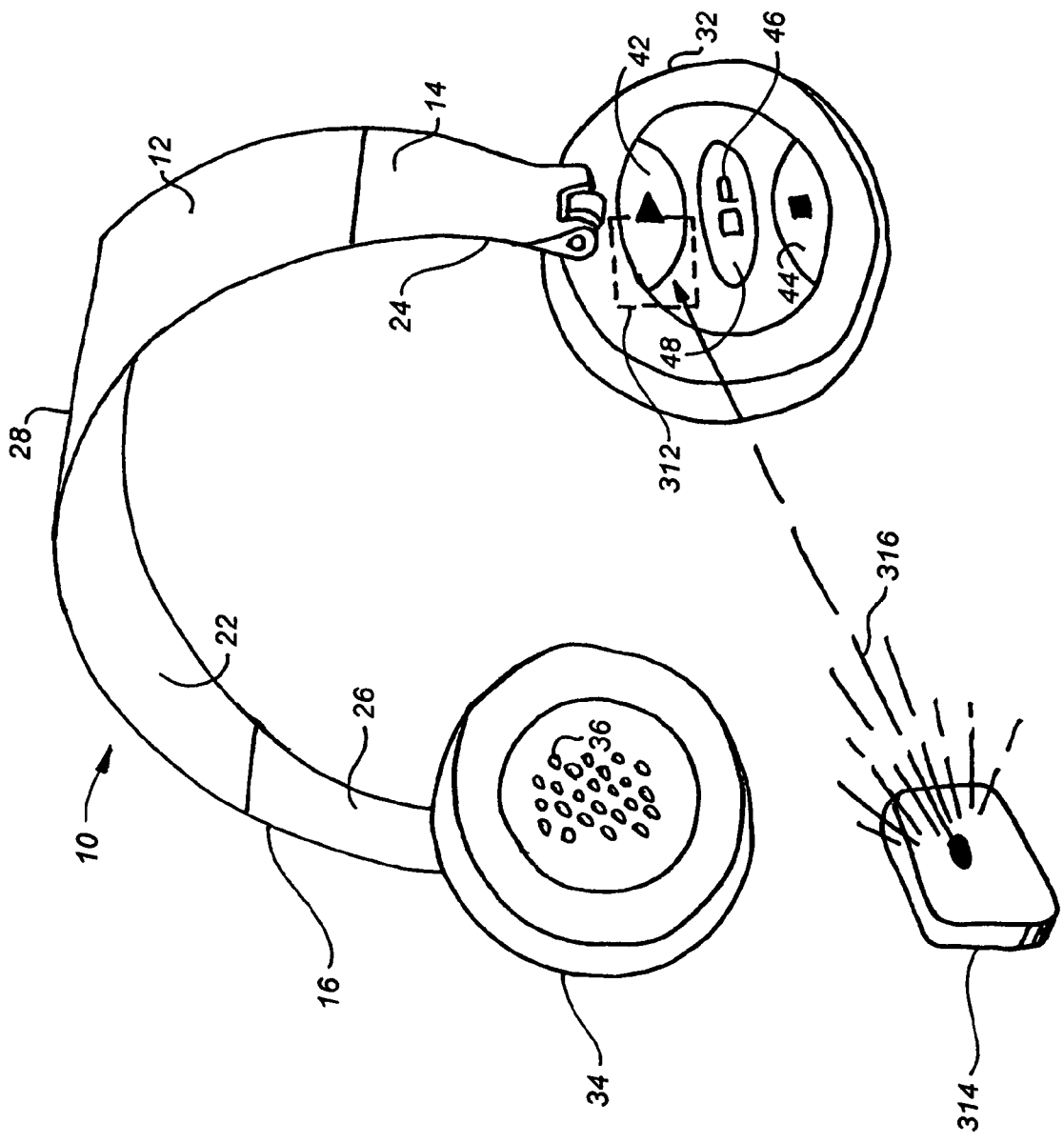
FIG. 6 is a perspective view illustrating the incorporation of a radio frequency identification device (RFID) in the headphones of FIG. 1; and, FIG. 7 is a perspective view illustrating the transport of a patient from one medical procedure to the next, wearing headphones in which a RFID has been incorporated.

FIG. 6 illustrates an RFID 312 incorporated in headphones 10. The RFID may be either a receiver or transceiver.

The receiver is only able to receive a signal, such as a signal from a fixed location station 314 that signals a command to the RFID. The signal is processed by the IC 214. The signal from station 314 can, for example, change the music selection in headphone 10 from pre-op to op, op to post op, etc.

The transceiver can both receive and transmit signals. The transceiver can receive a signal from a fixed location station 314 to change the music selection in headphones 10 from pre-op (pre-operation) to op (surgery), op to post-op, etc. Transceiver can then signal station 314 to identify the patient entering surgery by using a pre-entered numeric patient code. Station 314 transmits this information to a computer at a nurse's station or other desired location in the medical facility. This type of patient identification tracking system is utilized by many hospitals or medical institution, although not in conjunction with headphones or other apparatus that provides music to patients.

If desired, the RFID 312 can interact with GPS (Geo-Position Synchronous) systems to continuously track the location of doctors and patients. Such systems are currently in use at some hospitals and medical institutions, although not in conjunction with headphones or other apparatus that provides music to patients.

Figure 7:
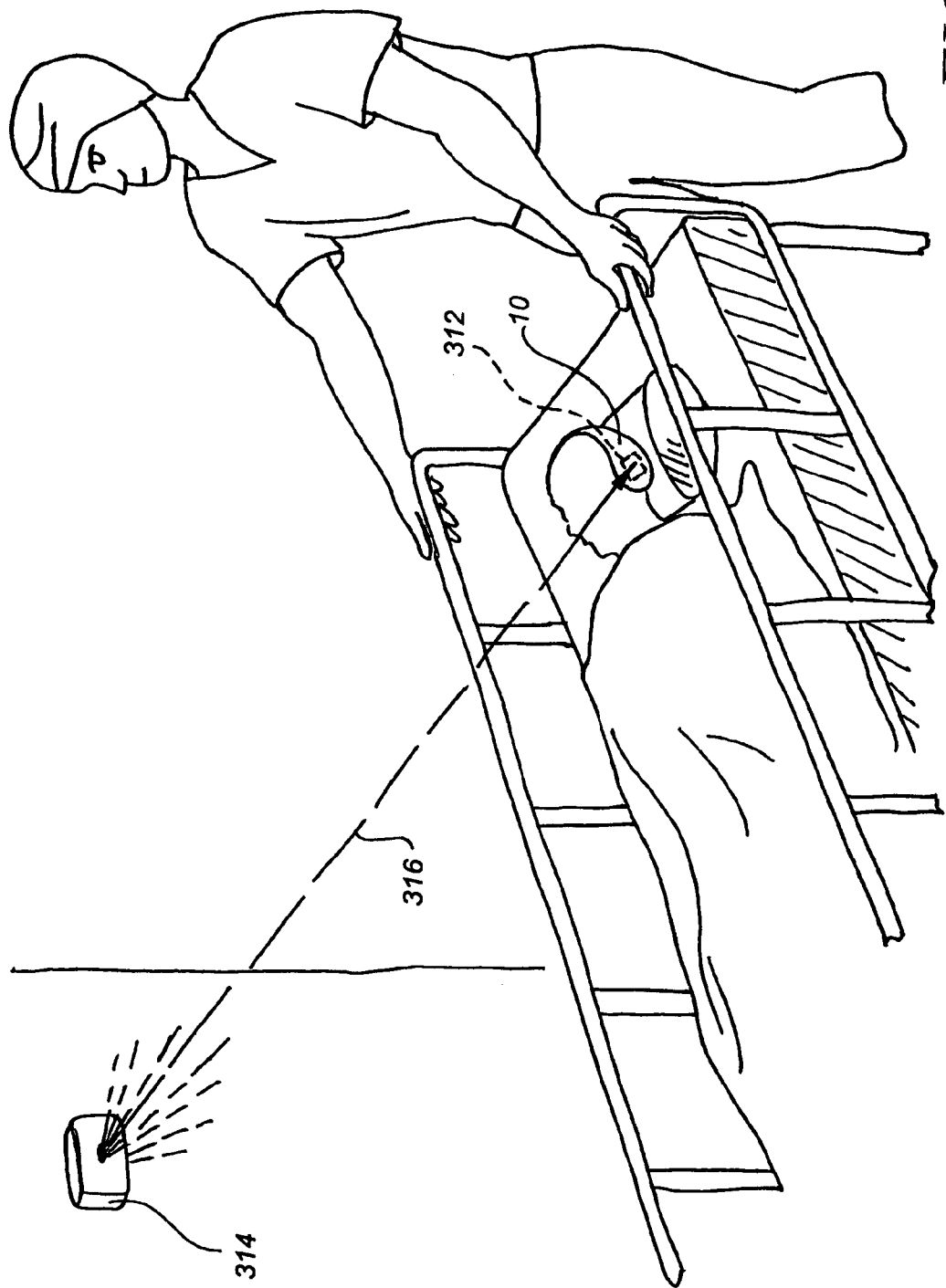

The headphones 10 in FIG. 7 include an RFID 312 that receives a signal 316 from fixed station 314. Station 314 detects the nearby presence of RFID 312 and issues command 316 via RF to the headphones 10 to change (index ahead one to the next music selection, or index ahead two, three, etc. to the next music selection) the music selection to correspond to the patient's next destination. If the patient is, for example, leaving the operating room and the next stage in the patient's medical procedure is post-op, station 314 is located in the hospital at a point intermediate the operating room and post-op, station 314 detects the RFID 312 as the patient is wheeled past station 314, and station 314 signals RFID 312 that the operation phase is over, that the patient is now headed to post-op, and that the "post-op" music loop should begin to play. Similar fixed stations 314 can be placed at desired locations in the hospital or medical facility intermediate pre-op and op, and intermediate post-op and general recovery.

As would be appreciated by those of skill in the art, music can be played for and delivered to a patient using apparatus other than headphones. Earphones of the type commonly found with iPODs or CD players can be utilized. These earphones are small and fit into the outer ear of a patient. One or two, as desired, earphones can be utilized for each patient. If necessary, an earphone can be placed in one ear and an earplug can be placed in the patient's other ear. When earphones are utilized, they are connected to a separate control unit that is secured to the table upon which the patient reclines. The control unit can include control buttons, knobs, display screens comparable to those shown in FIG. 1 on earphones 10. Or, the control unit can be located remote from the patient and earphones and transmit music to the earphones. Alternatively, a speaker can be mounted on the table or bed upon which the patient is reclining. The speaker is adjacent the patient's ear and transmits music into the patient's ear. When the patient is in a hospital room, the music may be played over a speaker located at a desired location in the room. In the operating room, however, it is desirable to play one kind of music for the patient and another for the surgeon and attending assistants. While relaxing music is played for the patient, a more upbeat music is often preferred by the surgeon or surgical team and is played over a speaker in the operating room so the music can be heard by the entire surgical team. Consequently, the patient's music is "piped into" the patient via headphones or other means that tends to block out the surgeon's music and that tends to prevent the surgical team from hearing the patient's music.

For purposes of the following discussion, earphones 10 include pre-recorded music track 512 for pre-op, music track 514 for op, music track 516 for post-op, and music track 518 for general recovery. Pre-recording musical tracks helps eliminate the inadvertent choice of inappropriate music that normally is at odds with the objectives of the invention. Such inappropriate music typically includes dissonant music, music with frequent tempo changes, loud music, heavy metal rock, music including the sounds of a screaming hysterical audience, music inciting to riot, etc.

Pre-Surgery: Music Track 512

This music track functions to reduce the pulse, blood pressure, and/or respiration of a patient to a level less that the patient's normal pulse, blood pressure, and/or respiration.

A patient's normal pulse, blood pressure, and respiration are determined when the patient is sitting and has not, other than walking at a normal relaxed pace on a generally level surface, performed any exercise for at least the prior fifteen minutes that would normally increase the patient's pulse, blood pressure, and respiration. For example, if a patient walks around on a floor for fifteen minutes reading a magazine, taking notes, watching television, or talking on a cell phone then the patient has not performed any exercise that would normally increase the patient's pulse, blood pressure, and respiration. If a patient sits for fifteen minutes typing on a computer, reading a book, or talking on a phone, the patient has not performed any exercise that would normally increase the patient's pulse, blood pressure, and respiration. If the patient just ascended a flight of stairs, ran a hundred yard dash, played tennis, lifted weights, did pushups, etc. within the last fifteen minutes, the patient has performed exercise that normally would increase the patient's pulse, blood pressure, and respiration.

The music on track 512 can be any desired type of music including but not limited to vocal or instrumental, religious, jazz, classical, popular, etc. The music must, however, function to relax the patient by promoting the disengagement, relaxation, and "letting go" of the patient's voluntary muscles and/or by reducing the patient's pulse, blood pressure, and/or respiration to selected levels below the patient's normal levels. Consequently, music that accomplishes this function typically is slow, has a steady tempo, and is relatively soft-but can still be heard by the patient. This music may be specifically and carefully selected from all existing recorded music; or, may be specifically recorded for the use with the instant invention. If the patient has normal hearing, music with a volume of sixty decibels or less is preferred, where sixty decibels is comparable to normal conversation levels. Twenty decibels is comparable to whispering communication. If the patient is hard of hearing, louder music may be "soft" to the patient.

When appropriate relaxing music is played for a patient, the need to administer benzodiazepine or other drugs often is reduced or eliminated.

Surgery: Music Track 514

Music track 514 increases relaxation of the patient's voluntary muscles and/or reduces the patient's pulse, blood pressure, and/or respiration to selected levels below those attained when the patient listened to music track 512. Again, the music utilized can vary depending on the patient, but typically the music is slow, soft, and has a steady tempo. Slow movements of Baroque suites or sonatas or other instrumental music often are ideal. The music need not be familiar to the patient; however, it is important and preferred, although not necessary, that the "beat" of the music matches the desired target range for heartbeats per minute. This is known as Entrainment, which is generally defined as the process whereby two oscillating bodies (specific to the instant invention, the beat or tempo of the music as one oscillating body, and the beat of the patient's heart as the second oscillating body) to lock into matching phase, and thus synchronize into one phase. More specifically, this is known as Rhythmic Entrainment, a well documented phenomenon.

Post-Op: Music Track 516

Advantageously, patients who have utilized music tracks 512 and 514 often will have needed less anesthesia and will awaken sooner from surgery. Even more importantly, since less anesthesia is used the patient does not descend to deep levels of unconsciousness sometimes associated with "full" anesthesia, and, consequently, recovers and can be discharged more rapidly. The patient returns to the comfort and familiarity of his or her own home, reducing the cost of the hospital stay; and allowing the hospital to help more patients in the course of a 24 hour period.

Further, anesthesia is typically associated with side effects such as temporary cessation of peristaltic action and other bodily functions. When less anesthesia is utilized, the return to normal bodily function is quicker, and risk of anesthesia-related complications are reduced.

The music on track 516 functions to assist in increasing the patient's voluntary muscle activity and/or pulse, blood pressure, and/or respiration from levels achieved during surgery. The music typically is louder and faster than the op music, but is still relaxing and comforting to the patient and does not work the patient into a frenzy or into a depressed state. As is the case with the music on tracks 512 and 514 (and 518), the patient should enjoy listening to the music on track 516. The music should, if possible, help to make the patient happy and put the patient in a positive frame of mind.

Recovery: Music Track 518

Relaxing, comforting music is on track 518 and is played for the patient before meals and at bed time. A music therapist can, if desired, work with the patient to select music that best helps to overcome a patient's pain, anxiety, or depression.

As noted earlier, it is preferred, but not required, that each track 512, 514, 516, 518 continuously loop, or repeat, until a control button is used to index to a subsequent track. Such looping automatically avoids the problem of progressing to a subsequent track before a patient reaches the treatment station (pre-op, op, post-op, recovery) that is associated with the subsequent track.

The musical apparatus and methodology of the invention can be applied to scenarios other than surgery. Different musical performance can be utilized at selected times during other sequences of events. For example, a patient making an office visit to a physician may be provided with headphones that play a first kind of music while the patient waits to be called to the examination room, and may play a second kind of music while the patient is waiting in the examination room for the physician. Or, speakers or sounds systems other than headphones can be utilized to play one kind of music for a patient in the waiting room and another kind of music in the doctor's examination room.

Having described the presently preferred embodiments and best mode of the invention in such terms as to enable those of skill in the art to understand and practice the invention,

We claim:

1. A method to minimize the amount of anesthetic required during surgery on an individual by at least one surgeon, comprising the steps of:
   (a) determining the normal heart rate and normal respiration rate of the individual;
   (b) identifying primary music that, when the individual is reclining, produces for the individual
      (i) a first selected reduced heart rate less than said normal heart rate, and
      (ii) a first selected reduced respiration rate less than said normal respiration rate;
   (c) playing for the individual said primary music during a pre-op period in advance of the surgery while the individual is held in a pre-surgery area;
   (d) identifying secondary music different from and having a slower tempo than said primary music such that, when the individual is reclining, said secondary music produces
      (i) a second selected reduced heart rate less than said first selected reduced heart rate, and
      (ii) a second selected respiration rate less than said first selected respiration rate;
   (e) playing for the individual said secondary music while the individual undergoes surgery in a surgical area;
   (f) identifying tertiary music different from and having a faster tempo than said secondary music such that, when the individual is reclining, said tertiary music produces
      (i) a third selected reduced heart rate greater than said second selected reduced heart rate, and
      (ii) a third selected respiration rate greater than said second selected respiration rate; and
   (g) playing for the individual said tertiary music during a post-op period in a post-surgery area.

2. The method of claim 1, further comprising the steps of, while the individual is in surgery:
   (a) playing said secondary music for the individual out of ear shot of the surgeon; and,
   (b) playing music other than said secondary music for the surgeon out of ear shot of the individual.

3. The method of claim 1, wherein the individual is wearing headphones that deliver said primary music, said secondary music, and said tertiary music.

4. The method of claim 3, wherein said headphones which include a sterile cover.

5. The method of claim 3, wherein said primary music is on a first pre-recorded track stored on and comprising a part of said headphones and said secondary music is on a second pre-recorded track stored on and comprising a part of said headphones.

6. The method of claim 5, wherein said headphones include a manually operable control located on said headphones to switch from said first pre-recorded track to said second pre-recorded track, and said control is utilized to switch from said first pre-recorded track to said second pre-recorded track when the individual is moved from the pre-surgery area to the surgical area.

7. The method of claim 1, wherein, while the individual is moved from the pre-surgery area to the surgical area, said primary music is discontinued and the playing of said secondary music is initiated by the control station.

8. The method of claim 7, wherein, while the individual is moved from the surgical area to the post-surgery area, said secondary music is discontinued and the playing of said tertiary music is initiated by the control station.

9. The method of claim 1, wherein the individual is wearing earphones that deliver said primary music, said secondary music, and said tertiary music.

* * * * *

UNITED STATES PATENT AND TRADEMARK OFFICE
CERTIFICATE OF CORRECTION

PATENT NO. : 7,431,689 B2
APPLICATION NO. : 11/526895
DATED : October 7, 2008
INVENTOR(S) : Booty, Jr. et al.

It is certified that error appears in the above-identified patent and that said Letters Patent is hereby corrected as shown below:

Claim 4, col. 8, line 57: Delete the word "which"

Claim 7, col. 9, line 9: Change the word "the" to --a--

Signed and Sealed this

Eighteenth Day of November, 2008

JON W. DUDAS
*Director of the United States Patent and Trademark Office*